United States Patent [19]

Halstead

[11] Patent Number: 4,611,113
[45] Date of Patent: Sep. 9, 1986

[54] HEAT STRESS CALCULATOR

[76] Inventor: David K. Halstead, 2605 Klingle Rd., NW., Washington, D.C. 20008

[21] Appl. No.: 695,221

[22] Filed: Jan. 25, 1985

[51] Int. Cl.⁴ ............................................. G06C 27/00
[52] U.S. Cl. ................................ 235/78 R; 235/88 R
[58] Field of Search .................... 235/78 R, 88 R, 89 R

[56] References Cited

U.S. PATENT DOCUMENTS

| | | | |
|---|---|---|---|
| 3,635,398 | 1/1972 | Toni | 235/88 R |
| 3,698,630 | 10/1972 | Dick et al. | 235/78 R |
| 3,721,007 | 3/1973 | Banner | 235/78 N X |

Primary Examiner—Benjamin R. Fuller

[57] ABSTRACT

The Heat Stress Calculator is a manually operated, mechanical computer and program for determining human thermal discomfort or heat stress, reported as an equivalent heat stress temperature (HST), for any given summer air temperature, relative humidity, wind velocity, sky condition, time-of-day, terrain, and individual physical activity level. The calculator consists of six circular and partial discs concentrically mounted for adjustment of their scales by rotation to various positions relative to each other and to stationary front and back windowed panels. The Heat Stress Temperature is the equivalent air temperature under standard moderate thermal and activity conditions that would result in the *same* heat stress produced by the actual conditions experienced. Under these standard conditions, the equivalent heat stress temperature represents a constant sweat rate—sweating being a principle indicator of thermal discomfort—and is read from isohids (lines of constant sweating) plotted on a grid of the body's *heat load* which must be dissipated by the evaporation of sweat, to the environment's *cooling capacity* to perform this evaporation. The body's evaporative heat load requirement is computed as the sum of heat generated by the level of physical activity plus solar heat gain, less heat loss by convection. Solar heat is computed by aligning the observed sky condition with the time-of-day, and then adjusting for terrain. Convective cooling is computed by aligning wind velocity with the observed air temperature (line) on a wind velocity-convective cooling grid. The environment's evaporative cooling capacity is computed by setting wind velocity, and then aligning relative humidity with the observed air temperature (line) on a humidity-evaporative cooling capacity grid.

8 Claims, 14 Drawing Figures

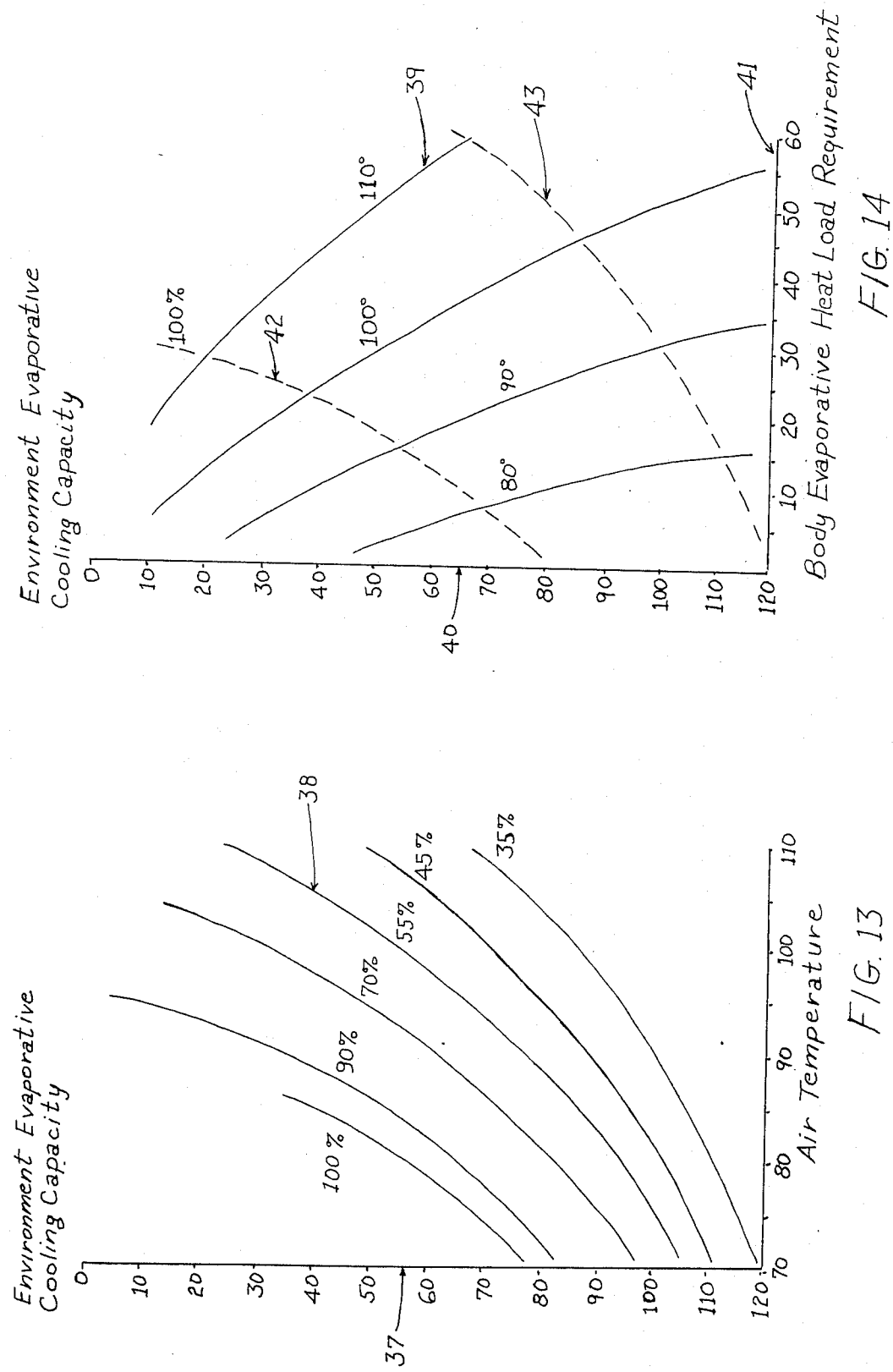

HEAT STRESS CALCULATOR

SUMMARY OF THE INVENTION

A principal objective of the present invention is to program the multiple formulas of physiological response to the thermal environment in a hand operated circular sliderule type mechanical computer which may be used for determining thermal discomfort or heat stress in the human body. This programming involves appropriate simplification and combination of formulas and unique design of the sliderule type mechanism to permit relatively quick and easy introduction of the input variables and computation.

A second objective of the invention is to report heat stress in a meaningful and readily understandable manner. The level of heat stress, or thermal discomfort experienced by the human body, is thus reported as an equivalent temperature to which one can readily relate rather than an arbitrary and unfamiliar index number requiring definition. Heat Stress Temperature (HST) is the equivalent air temperature under moderate weather conditions and personal physical activity that would result in the *same* thermal discomfort produced by the actual temperature and weather experienced and activity performed. The standard conditions are: relative humidity, 35 percent; wind velocity, 2.5 mph; sun, haze; time, 1 pm; terrain, grass; and physical activity, walking 2.5 mph. No heat stress occurs under these standard conditions for an average male dressed in light summer clothing at an air temperature of 70° F. The equivalent Heat Stress Temperature is further made meaningful by identifying environmental sensation (e.g., warm, hot, etc.) and body strain (e.g., moderate, severe, etc.) associated with rising HSTs.

A third objective of the invention is to utilize the body's sweat rate as the best single indicator of heat stress, and to establish a functional relationship of sweat rate with the two principal governing factors—the body's evaporative heat load requirement and the environment's evaporative cooling capacity—both factors measurable in terms of observed thermal environment and physical activity conditions. This relationship is established by use of a psychometric chart on which isohids of constant sweat rate are plotted. The chart's ordinate scale of air vapor pressure is converted to a scale of associated environment evaporative cooling capacity at standard wind velocity; the abscissa scale of air temperature is converted to a scale of associated body evaporative heat load requirement at standard wind velocity, sky condition, time-of-day, terrain, and physical activity level. With this conversion, the isohids become lines of constant equivalent temperature.

A fourth objective of the invention is to calculate and report in meaningful terms, the basic relationship which establishes human heat stress—the absolute level and relative ratio of the body's evaporative heat load requirement and the environment's evaporative cooling capacity. The absolute values calculated are reported in small windows on the front of the calculator. The heat transfer rates for heat load and cooling capacity are expressed as a percent with 100 equal to the energy expended in jogging at a 10 minute per mile pace.

A fifth objective of the invention is to facilitate operator use, yet retain valid heat stress measurement, by limiting the input variables to observable and measurable key environmental factors and incorporating other key varables into the programmed formulas. Thus inputs are limited to seven: air temperature, relative humidity, wind velocity, sky condition, time-of-day, terrain, and individual physical activity level. Heat storage within the body and work performed are programed as variables within the computer formulas. Pulminary ventilation, rest breaks, clothing, and body sex, weight, and age are programmed as constant factors.

A final objective of the invention is to facilitate operator use by scaling the input variables in units or terms which are readily understood, and may be measured or estimated by the user. Physical activity is therefore described in terms of severity (e.g., light, moderate, heavy) with specific common activities identified on the severity scale as benchmarks (e.g., walking 4 miles per hour). Sky conditions are described in terms of cloudiness (e.g., clear, haze), and shadow status (e.g., distinct, soft).

This invention is a hand operated, circular sliderule type mechanical computer which can be used for quickly and easily determining heat stress in the human body (reported as an equivalent temperature) based on inputs of observed air temperature, relative humidity, wind velocity, sky condition, time-of-day, terrain, and on the individual's physical activity level. The calculator consists of six circular cardboard or plastic discs fastened at the center and mounted in a housing consisting of stationary front, intermediate, and back panels. All formulas used in calculating the equivalent Heat Stress Temperature are programmed in the scales, grids, and indicator arrows printed on the calculator. Rotation and alignment of input values on these measuring elements perform the calculations.

It is integral to the front panel at the bottom along common line A—A and folded or attached along this line against the front panel with the intermediate panel in-between.

Figure 3:
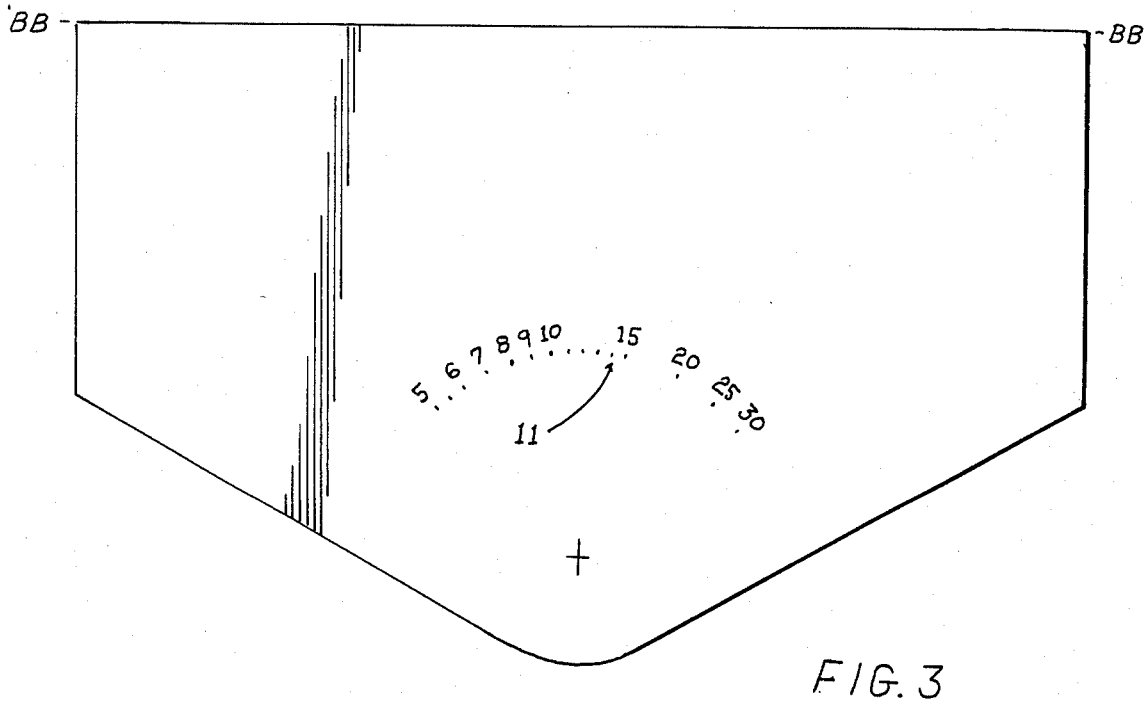

FIG. 3 is the intermediate panel of the body read from the back of the calculator. It is integral to the front panel at the top along common line B—B and folded or attached along this line against the front panel.

Figure 4:
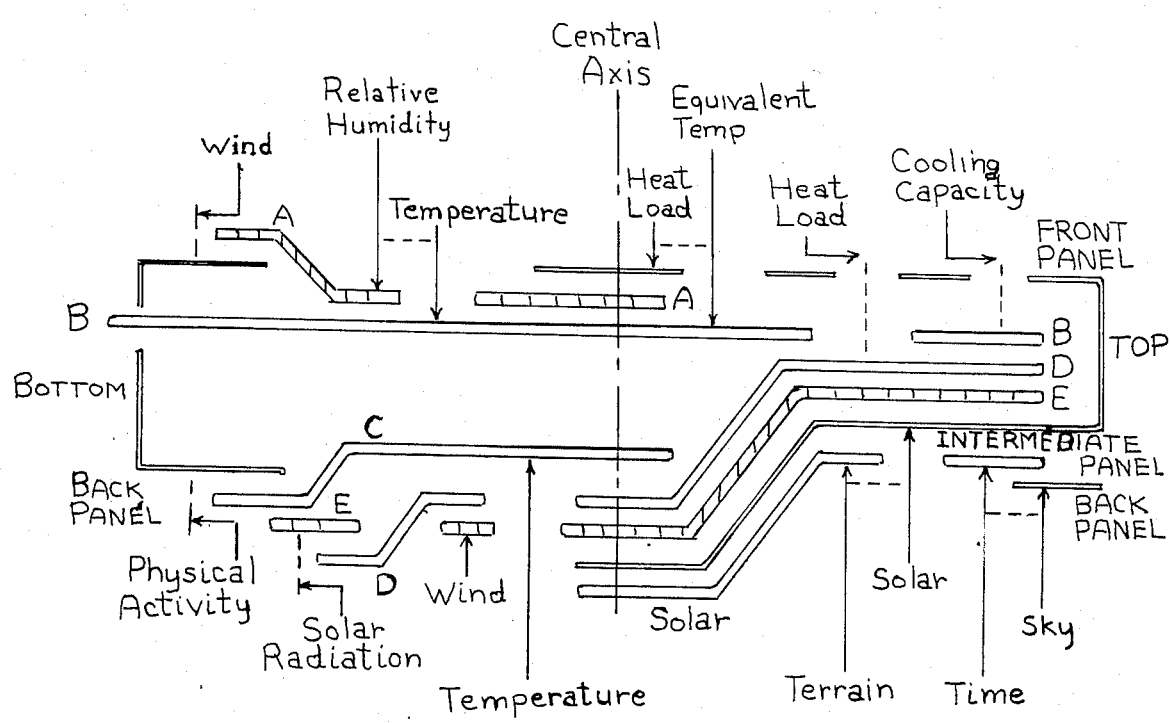

FIG. 4 is a schematic diagram (not to scale) of a cross section top-to-bottom view of the calculator to show the interrelationships of the circular discs and body panels when assembled. The bend in the discs is grossly exaggerated to allow the front-to-back disc and panel positions to be clearly illustrated.

Figure 5:
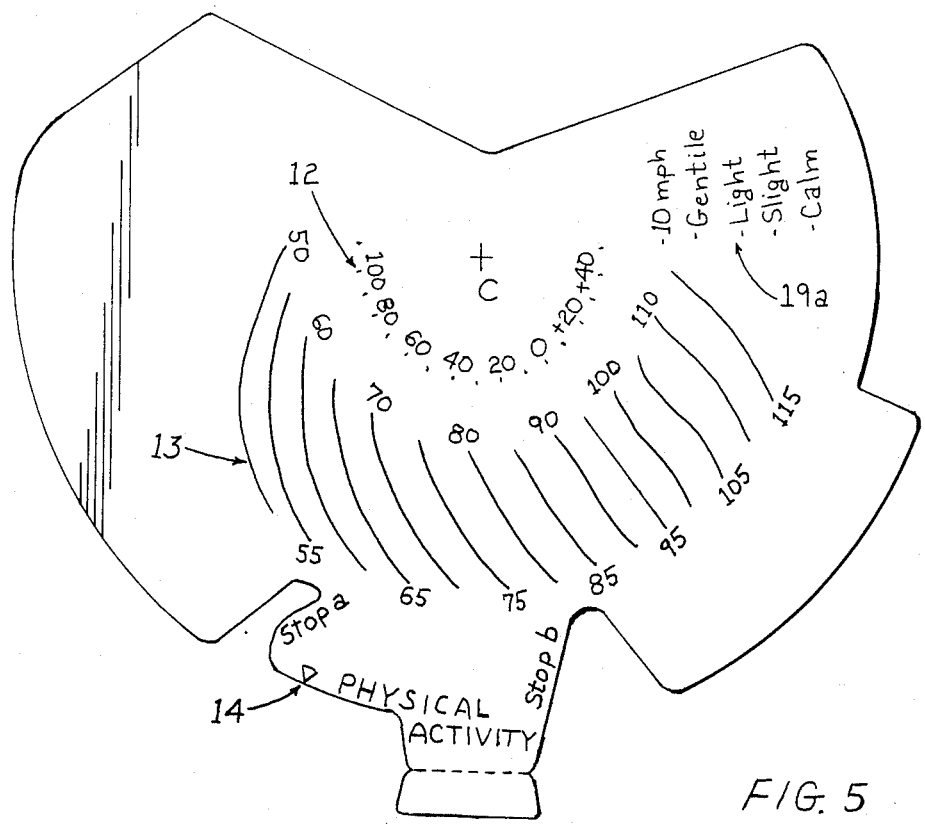

FIG. 5 is the first disc element titled "Wheel C" which is read from the back of the calculator and is located directly below the back panel. Wheel C is turned by a tab which extends above and over the back panel.

Figure 6:
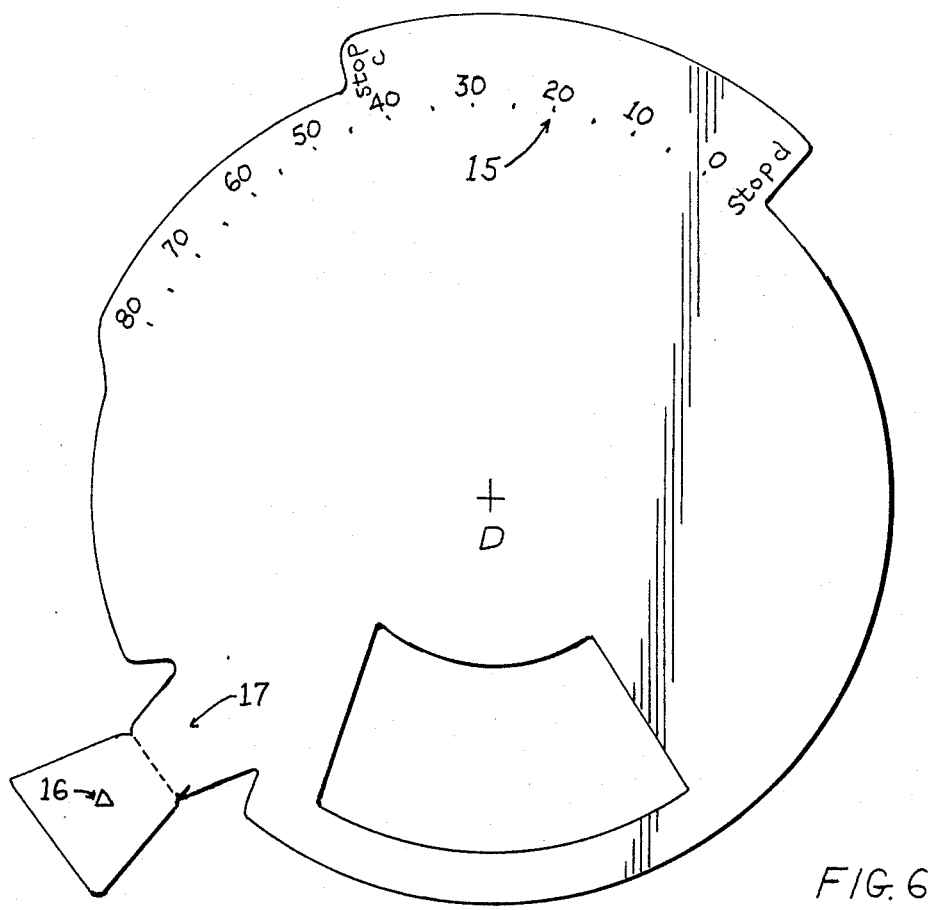

FIG. 6 is the second disc element titled "Wheel D" whose pointer is read from the back of the calculator and whose heat load scale is read from the front of the calculator. Wheel D is located directly above wheel C with the top half located below the intermediate panel of the body and the bottom half located above the back panel of the body. Wheel D is turned by a tab which extends through a slot in disk E.

Figure 7:
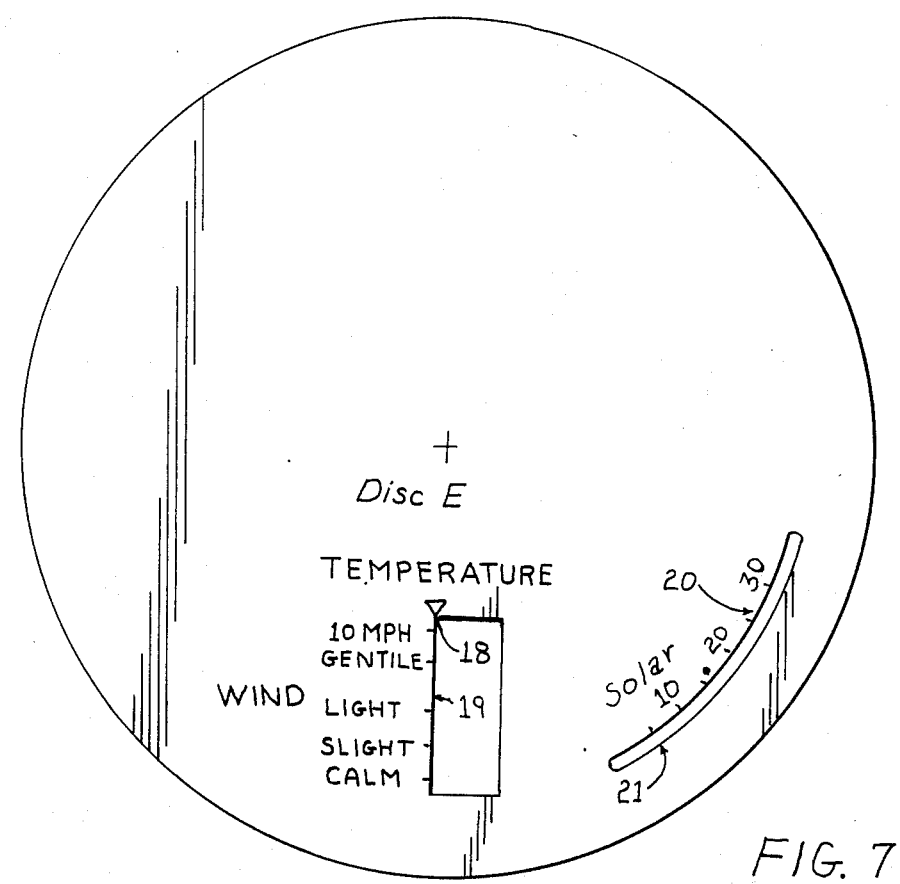

FIG. 7 is the third disc element titled "Disk E" which is read from the back of the calculator and is mounted immediately above wheel D with the upper half located directly below the intermediate panel of the body. Disk E itself is turned.

Figure 8:
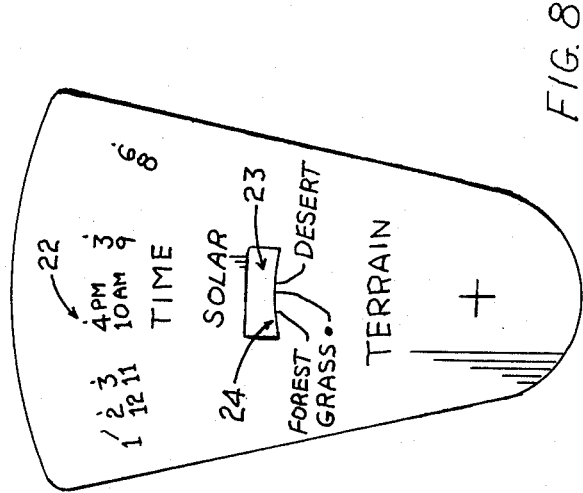

FIG. 8 is the fourth disc element titled "Solar" which is read from the back of the calculator and is located directly below the top of the back panel. The Solar element itself is turned.

Figure 9:
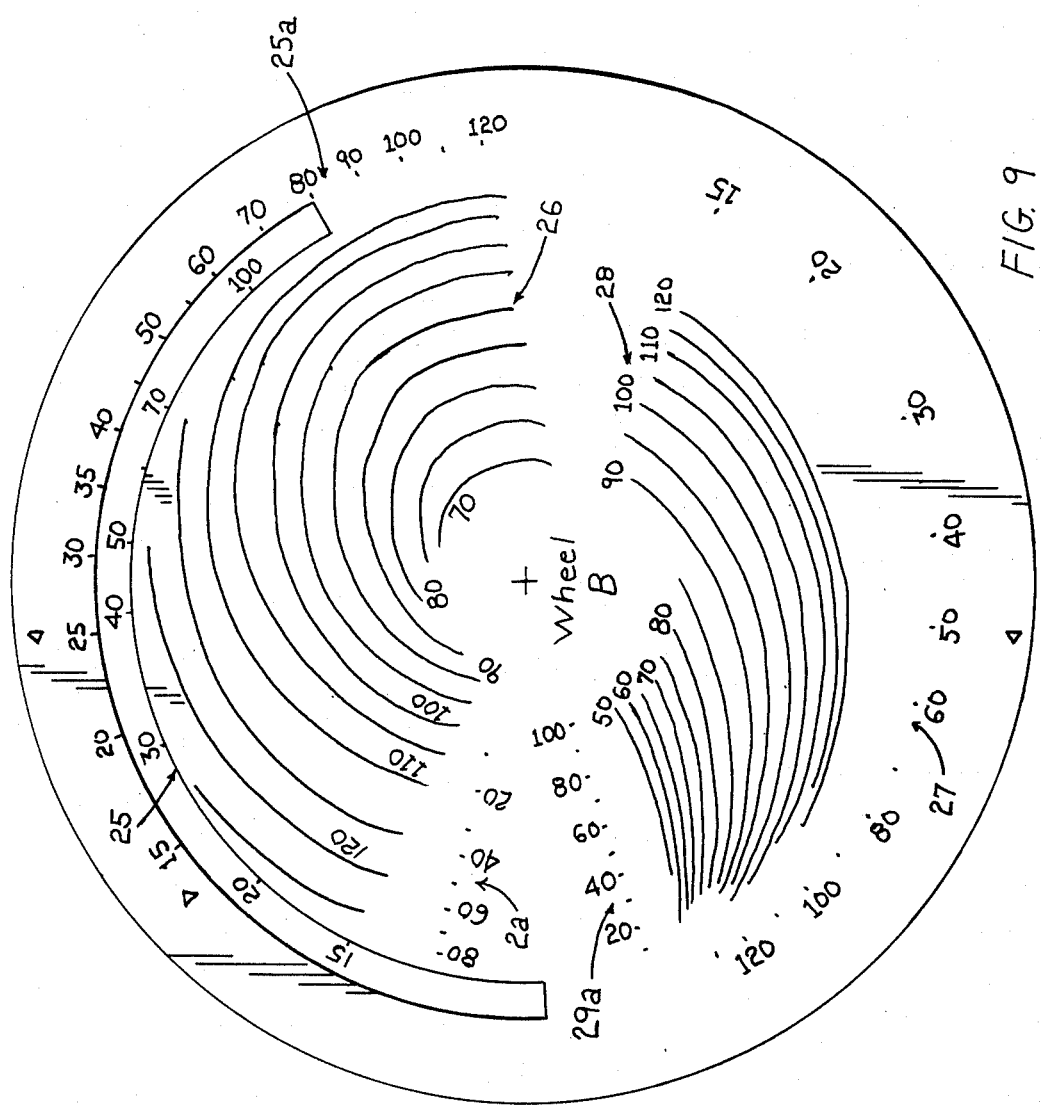

FIG. 9 is the fifth disc element titled "Wheel B" which is read from the front of the calculator and is located directly below wheel A. The outer edge of wheel B is rotated at a front and rear panel cutout at the left side of the calculator.

Figure 10:
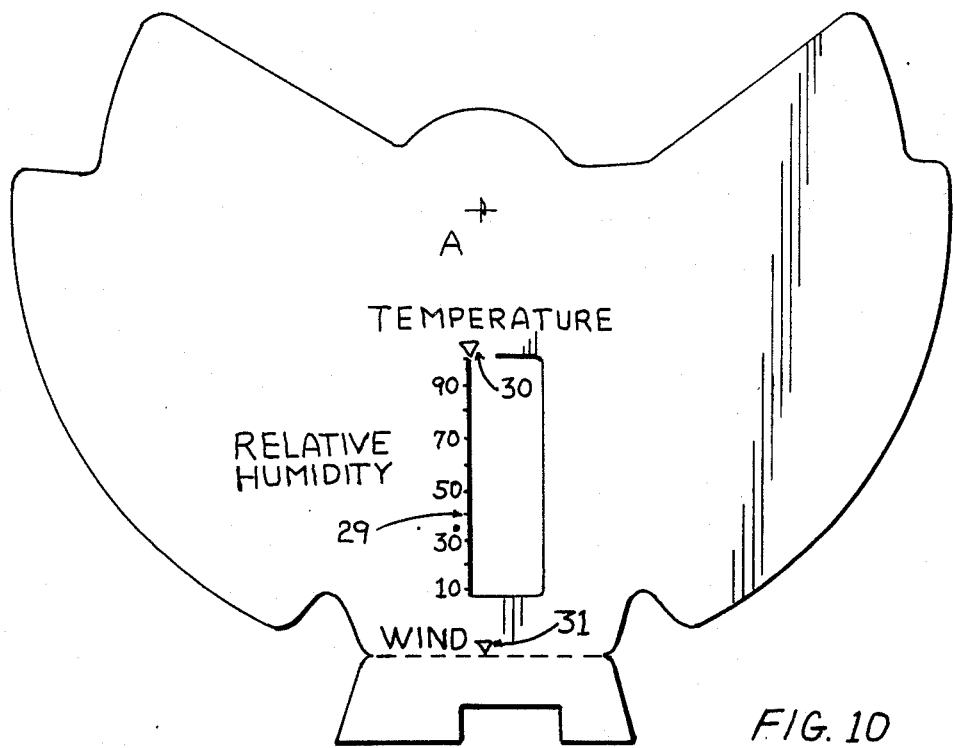

FIG. 10 is the sixth disc element titled "Wheel A" which is read from the front of the calculator and is located directly below the front panel. Wheel A is turned by a tab which extends above and over the front panel of the calculator body.

Figure 11:
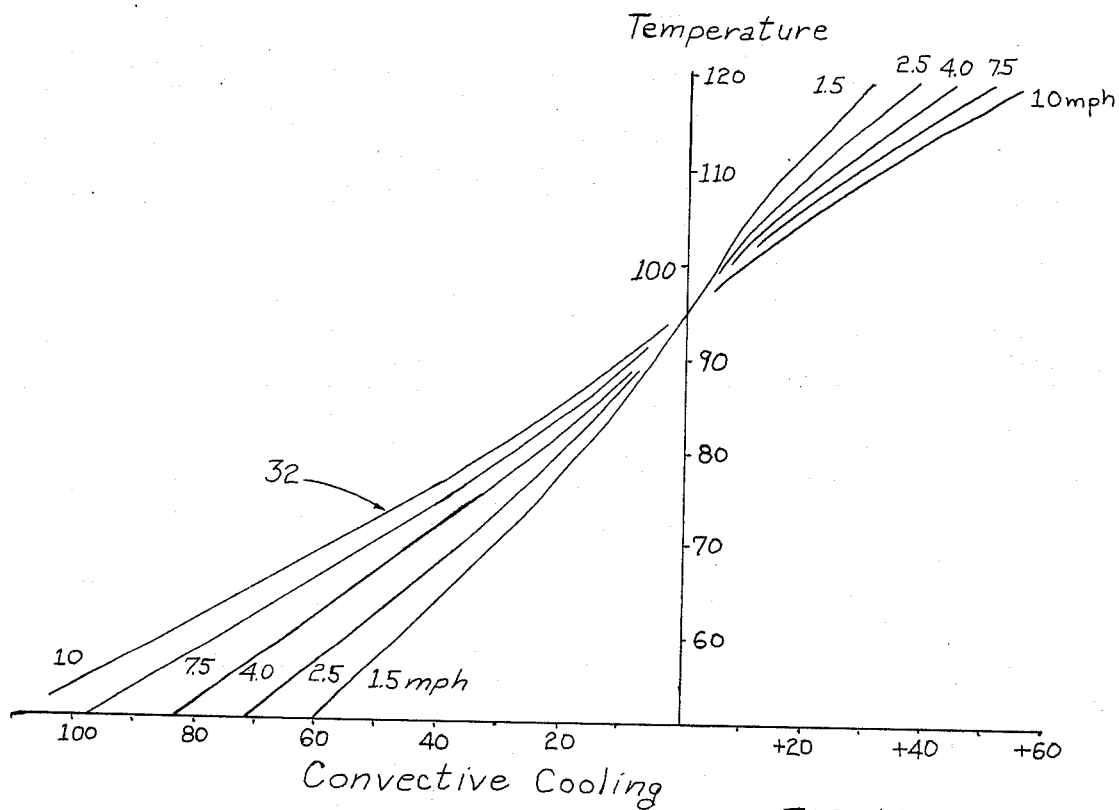

FIG. 11 represents, in schematic form, a graphical plot of convective cooling as a function of wind velocity and air temperature.

Figure 12:
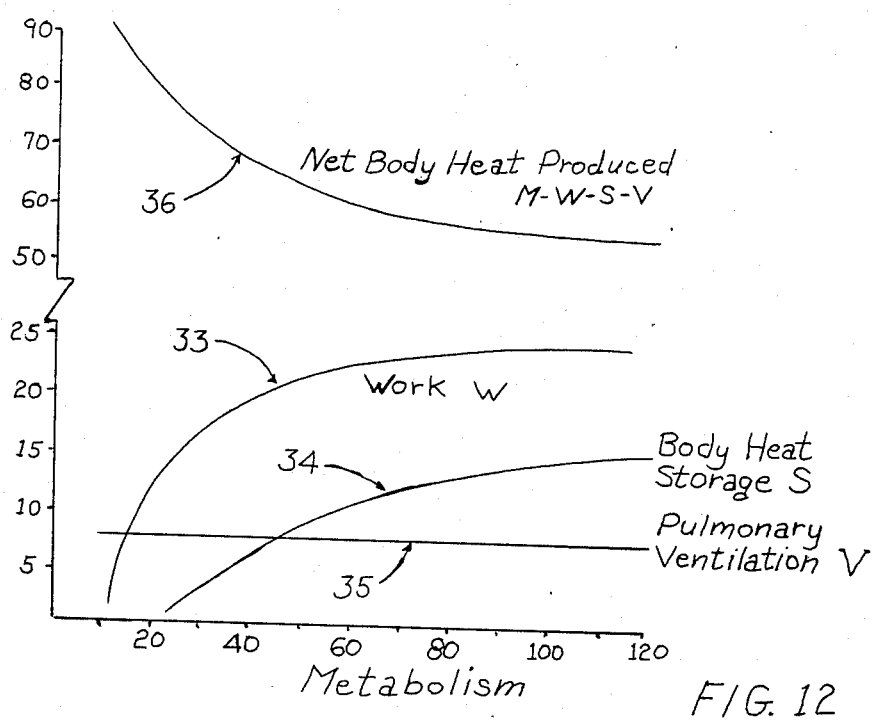

FIG. 12 represents, in schematic form, a graphical plot of the basic relationships of metabolism, work, body heat storage, heat loss through pulminary respiration, and net body heat production.

FIG. 13 represents, in schematic form, the relative humidity lines of a psychometric chart with air temperature abscissa and environment evaporative cooling capacity at standardard wind velocity 2.5 mph substituted for the vapor pressure ordinate.

FIG. 14 represents, in schmematic form, a psychometric chart with an overlay of isohids (lines of constant sweating) which represent equivalent temperture lines when the abscissa is converted to body evaporative heat load requirement, and ordinate converted to environment evaporative cooling capacity, both under standard conditions.

The "cut out" labels on all drawings indicate areas that are either cut out if the pieces are made of cardboard, or are clear or cut out if the pieces are made of plastic.

DESCRIPTION OF THE PREFERRED EMBODIMENT

The heat stress calculator of the present invention consists of three attached body parts—front panel (FIG. 1), rear panel (FIG. 2), and intermediate panel (FIG. 3), which serve as a stationary housing for a central axis for six concentric full or partial discs (FIGS. 5–10), which are turned to record thermal environment conditions and physical activity level as inputs. The process of recording the input data automatically computes heat stress as an equivalent temperature under standard moderate thermal (weather) and activity conditions. The standard conditions are: relative humidity, 35%; wind velocity, 2.5 mph; sky, haze; time-of-day, 1 pm; terrain, grass; and physical activity, walking 2.5 mph. These standard conditions are represented by green dots on the scales involved.

Also standardized are sex (male), age (youth to middle), body build (slight to medium), clothing (cotton short or long sleeved shirt, open at collar, cotton short or long trousers, light socks and shoes—the clothing ensemble having a clo-value of 0.5), and hourly rest breaks during physical exercise.

The body panels and discs are made of laminated cardboard approximately 0.016"–0.024" thick or plastic approximately 0.020" thick. The panels are attached at their edges, as required, by staples, glue, or other appropriate bond to establish a rigid body.

The uniqueness of this invention is the computer mechanism and scale program which establish the relationships of the three body panels and six rotating concentric discs and their scales so as to compute by sliderule type procedures specially developed formulas involving linear, exponential, and grid functions to derive a final equivalent temperature output from seven input variables (air temperature, relative humidity, wind velocity, sky condition, time-of-day, terrain, and physical activity level), two formula programmed variables (work and body heat storage), and four fixed factors (pulminary ventilation cooling, rest breaks, clothing, and body condition).

All scales, marks, and arrows printed on the parts of the calculator are positioned in such a manner that when the parts are assembled the scales, marks, and arrows of any two or more parts involved in a sliderule type computation of a given formula are calibrated in common angular units and are located immediately adjacent to each other for direct alignment and scale reading.

Heat transfer rates are normally measured in watts per square meter of body skin surface (watts/m$^2$). To improve operator understanding of the relative magnitude of heat involved, all scales of heat transfer on the calculator are expressed as a percent of 100 equal to the heat transfer rate during the maximum evaporative cooling of the body under ideal thermal conditions of low temperature and humidity, and high wind velocity. This transfer rate of 435 watts/m$^2$ may be understood as roughly the energy required to jog at a 10 minute per mile pace. Thus, any heat transfer rate can be judged relative to this known energy expenditure rate of 100 percent. While this measure of the absolute level of heat transfer is meaningful to the operator, the relative values of heat transfer involved are critical to the programming of the calculator.

Briefly stated, the calculator computes, as a function of air temperature (dry bulb), the body's evaporative heat load requirement and the environment's evaporative cooling capcity under standard thermal and activity conditions, to establish a grid for isohid lines of constant sweating and comfort which may be interpreted under the standard conditions as lines of equivalent temperature.

The formula programmed for the body's evaporative heat load requirement is: heat gain from solar radiation, plus net body heat production from physical activity, minus heat loss from convective cooling. The scales involved—referred solar heat gain 20 (FIG. 7), net body heat produced 9 (FIG. 2), convective cooling circumference 12 (FIG. 5), and body evaporative heat load requirement 15 (FIG. 6), are recorded in common linear angular units (12°=43.5 watts/m$^2$ or 10% heat transfer rate) for sliderule type addition.

Figure 2:
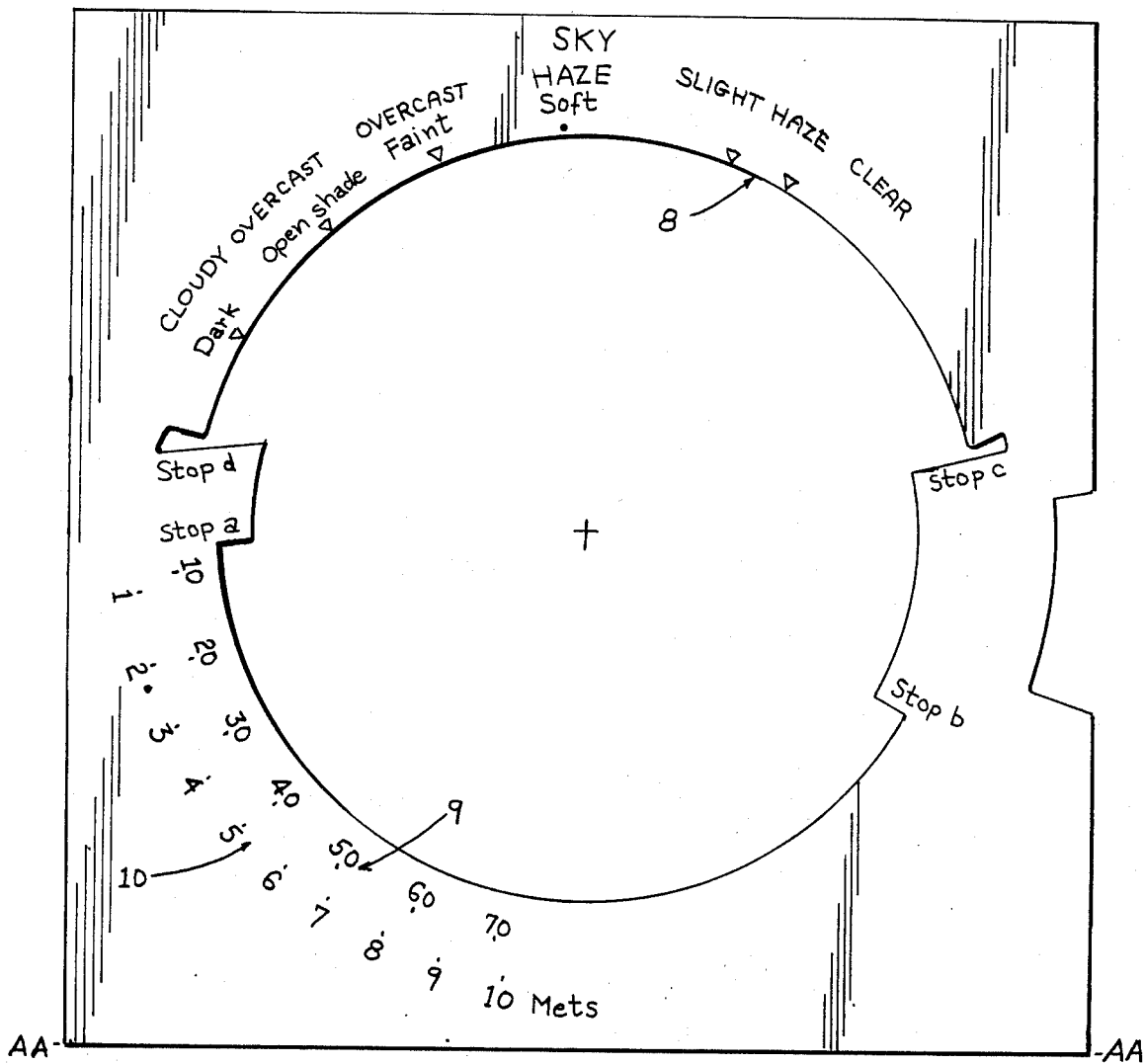
FIG. 2 is the back panel of the body of the calculator, read from the back.

The heat load from solar radiation is calculated in STEP 1 by the operator turning the solar radiation disc (FIG. 8) to align the time-of-day 22 with the sky condition 8 on the body back panel (FIG. 2). The, in STEP 2 the operator reads the solar radiation heat gain 11, printed on the intermediate body (FIG. 3), in window 23 on the solar disc (FIG. 8) opposite the terrain condition 24, and transfers this reading to the referred solar heat gain scale 20 on disk E (FIG. 7), by aligning the solar arrow 16 on tab 17 on wheel D (FIG. 6) with the read value. (Tab 17 on wheel D fits through the arcuate slot 21 on wheel E.) In STEP 3, net body heat produced 9 (FIG. 2) from physical activity is calculated by aligning the physical activity arrow 14 printed on wheel C (FIG. 5) with the physical activity level scale 10 printed on the body rear panel (FIG. 2).

Figure 1:
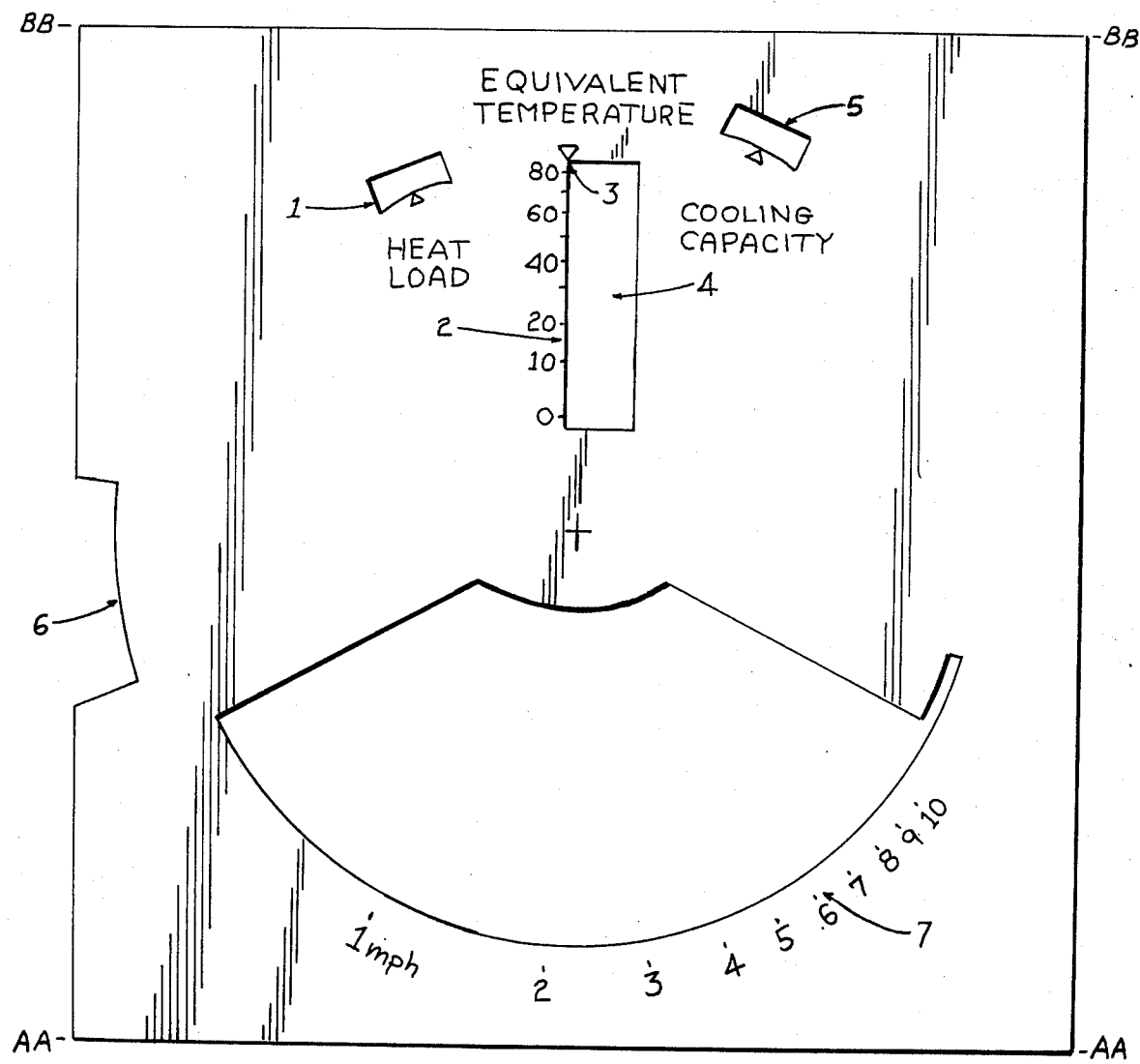
FIG. 1 is the front panel of the body of the calculator, read from the front.

Convective cooling is computed in STEP 4 by aligning the 1st input wind velocity 19 printed on disk E (FIG. 7) with air temperature from the 1st input air temperature line overlay 13 on the grid of wind velocity radius 19a vs convective cooling circumference 12 printed on wheel C (FIG. 5). The alignment occurs at the left edge of the window directly below the 1st input temperature arrow 18. The computed body evaporative heat load requirement, equal to solar heat gain plus net body heat produced from physical activity minus convective cooling, is read from scale 15 on wheel D (FIG. 6) through the left window 1 on the body front panel (FIG. 1).

Referring now to FIGS. 2, 3, and 7, the sky condition 8, printed at the top of the stationary back panel (FIG. 2), the time-of-day 22, and terrain 24 scales printed on the rotating solar disc (FIG. 8), and the solar radiation heat gain scale 11 printed on the stationary intermediate body panel (FIG. 3), are recorded on angular logarithmic adjacent (when assembled) scales for sliderule type muliplication based on average attenuation of solar heat load in the human body by these three factors (sky, time, and terrain). The formula programmed is: solar heat load=maximum solar heat load (127 watts/m$^2$ or 29.2% heat transfer rate)$\times$sky attenuation$\times$time-of-day attenuation$\times$terrain attenuation. The attenuation rates for sky conditions are: clear, 100%; slight haze, 85%; haze, 54%; overcast, 38%; cloudy overcast or open shade, 27%; and cloudy overcast or dark shade, 18.5%. The time-of-day (daylight savings time) attenuation rates are: 1 pm, 100%; 2 pm or 12 noon, 95%; 3 pm or 11 am, 87%; 4 pm or 10 am, 75%; 5 pm or 9 am, 60%; and 6 pm or 8 am, 46%. The attenuation rates for terrain are: desert or city streets, 104.8%; grass and scattered trees, 100%; and forests, 92%.

The grid (FIG. 5) of wind velocity radius 19a vs convective cooling circumference 12 with 1st input air temperature line overlay 13 used to compute convective cooling, is an angular derivation of the plot illustrated in FIG. 11. The plot of convective cooling (C) is initially estimated from the formula $C=5.0\ V^{.3}$ (skin temperature—air temperature) in watts/meter$^2$, where wind velocity (V) is the effective wind velocity on the skin surface in miles per hour and skin (95° F.) and air temperatures are in degrees Fahrenheit. The resulting wind velocity lines 32 are modified to account for known empirical evidence and their steepness is increased slightly as air temperature approaches 95° F. to account for slightly rising skin temperature. Note that when air temperature equals skin temperature of 95 degrees F. there is no convective cooling, and that at higher air temperatures heat is *gained* by the body from air convection.

Strictly for layout design and not a programmed formula, the 1st input wind velocity scale 19 (FIG. 7) and co-aligned wind velocity radius 19a of the wind velocity versus convective cooling grid (FIG. 5), are scaled proportionate to wind velocity to the 0.3 power to provide simple physical spacing on both scales and the 1st input temperatue line overlay consistent with the functional relationship involved.

Referring now to FIG. 2, printed on the lower left of the body back panel is a linear physical activity level scale 10 reading in mets (1 met=58.2 watts/meter$^2$) of energy expenditure (metabolism) and further described in terms of severity (e.g., sedentary, light, moderate). The scale also contains benchmark known physical activities (e.g., standing, 2½ mile per hour walk, 10 minute mile run). Although reading in internal energy expenditure (metabolism) to permit the operator to enter the *exertion* aspect of physical activity as an input, the scale is calibrated to measure net body heat production rate (metabolism less energy expended for work, energy loss through publmonary ventilation, and energy stored) as measured on the adjacent net body heat produced scale 9. These relationships are shown in FIG. 12.

Referring to FIG. 12, work performed 33 (change in kinetic and potential energy of the body plus any external load movement and friction) (W) is an elliptically shaped exponential function of metabolism (M). Expressed as a percent of metabolism, work begins at a sedentary activity level, increases at a decreasing rate, and levels, approaching a maximum of approximately 24 percent of body metabolism at high activity levels.

Storage (S) of heat in the body is also an elliptically shaped exponential function 34 of metabolism reaching a maximum of 15 percent of metabolism at high activity levels. At exhausting physical activity levels (10 mets or more) this 15 percent storage rate approaches 100 watts/meter$^2$, a rate which will store heat to the body's capacity in one hour. Since this storage rate is programmed into the calculator and must be maintained, the physical activity level entered must include rest breaks every hour to dissipate body heat to renew storage capacity.

Pulmonary ventilation (V) 35 or heat loss through respiration equals a relatively constant average 7.5 percent of metabolism.

The rate of net body heat produced (M-W-S-V) 36 is derived from the curves of work, storage, and pulmonary ventilation, and is shown to decline exponentially as a percent of metabolism as physical activity increases.

The environment's evaporative cooling capacity is a function of air temperature, relative humidity (relative humidity and temperture establish air vapor pressure), and wind velocity. It is calculated in STEP 5 by aligning the 2nd input wind arrow 31 on wheel A (FIG. 10) opposite the observed velocity on the 2nd input wind velocity scale 7 on the body front panel (FIG. 1). The, in STEP 6, the operator turns wheel B (FIG. 9) through the cut-out 6 on the left side of the calculator front panel (FIG. 1) to align the observed 2nd input air temperature line 28 (on wheel B) with the observed relative humidity 29 on wheel A (FIG. 10). The alignment occurs at the left edge of the window directly below the 2nd input temperature arrow 30. The resulting computed cooling capacity is read from the environment's evaporative cooling capacity scale 25a printed on wheel B (FIG. 9) opposite the cooling capacity arrow in the right window 5 on the body front panel (FIG. 1).

The grid of relative humidity radius 29a vs environment evaporative cooling capacity circumference 27 with 2nd input air temperature line overlay 28 (FIG. 9) used to computer evaportive cooling capacity is an angular derivation of these three factors from the psychometric chart plot of lines of constant relative humidity 38 illustrated in FIG. 13. The environment's evaporative cooling capacity (E) 37 is substituted for the vapor pressure ordinate for a standard wind of 2.5 mph according to the formula: $E=101.84\ V^{.6}$ (skin vapor pressure—air vapor pressure) in watts/m² where skin vapor pressue equals 5.62 kpa (mm Hq). At standard conditions of 70° F. air temperature and 35% relative humidity, the standard wind velocity of 2.5 mph results in an evaporative cooling capacity of 522 watts/m² or a 120% heat transfer rate. Attenuation of evaporative cooling capacity by the formula for various selected 2nd input wind velocities relative to 2.5 mph used for wind scale 7 (FIG. 1) are: calm (1.5 mph), 73.3%; slight (2.5 mph), 100%; light (4 mph), 132.5%; gentle (7.5 mph), 193.3%; and 10 MPH, 230%. This attenuation is based on evaporative cooling capacity as an exponational function of wind velocity to the 0.6 power. Cooling capacities above 100 percent are theoretical and used to calculate the effects on evaporative cooling of combinations of relatively low temperature, humidity, and high wind speeds, and are utilized *only when the body's maximum effective sweat rate has not been reached.*

The 2nd input wind scale 7 (FIG. 1), and in FIG. 9 the environment's evaporative cooling capacity circumference scale 27 of the relative humdity vs cooling capacity grid with 2nd input air temperature line overlay, the environment evaporative cooling capacity circumference scale 25, and the environment evaporative cooling capacity scale 25a, are recorded in common logrithmic angular units for sliderule type multiplication. The relative humidity scale 29 (FIG. 10) and co-radial aligned relative humidity radius 29a (FIG. 9) of the relative humidity versus environment evaporative cooling capacity grid are scaled in linear proportion.

To determine equivalent temperature in STEP 7, the operator reads the computed body evaporative heat load requirement 15 printed on wheel D (FIG. 6) opposite the heat load arrow in the left window 1, on the front panel (FIG. 1). Then, opposite this heat load value on the referred heat load scale 2, the operator reads, directly below the equivalent temperature arrow 3, the equivalent Heat Stress Temperature from the adjacent equivalent temperture line overlay 26 seen through the center window 4.

Referring to FIG. 9, the grid of body evaporative heat load requirement radius 2a versus environment evaporative cooling capacity circumference 25 with equivalent temperature line overlay 26 printed on wheel B (FIG. 9) is an angular derivation of the isohids 39 (lines of constant sweating) plot on the psychometric chart illustrated schematically in FIG. 14. The isohids 39 represent equivalent temperature lines when the vapor pressure scale ordinate is converted to resulting environment evaporative cooling capacity 40 at standard wind velocity (2.5 mph); and the air temperature scale abscissa is converted to body evaporative heat load requirement 41 at standard wind velocity (2.5 mph), sky conditions (hazy), time-of-day (1 pm), terrain (grass), and physical activity level (walking 2.5 mph). Approaching and above the 100% relative humidity line 42, the isohids have been extended and modified slightly to establish equivalent temperature lines in this area. The equivalent temperature lines are labeled according to the temperature value where the isohid intersects the standard relative humidity line of 35 percent 43.

It is important here to cite the conditions under which there is no body evaporative heat load. Referring to FIG. 11, note that at 70° F. the standard conditions result in convective cooling of 37.6% heat transfer rate which exactly equals the body's net heat production walking 2.5 mph (21.8%) plus the solar heat gain under a haze sky (15.8%). Thus the body's evaporative heat load requirement is zero (no heat strain) at 70° F. The standard conditions have been selected to establish 70° F. as an easily recognizable temperature for no heat strain.

Critical to establishing this zero body evaporative heat load requirement at 70° F. are the following heat transfer relative ratios involved: solar heat gain at 1 pm, haze sun, and grass terrain, 1.00; net body heat produced from walking 2.5 mph, 1.38; and convective cooling at 70° F. and wind velocity 2.5 mph, 2.38. Other notable benchmarks where convective cooling equals the sum of solar heat gain (1.00) plus net body heat produced resulting in a zero body evaporative heat load requirement, occur for net body heat produced from standing, 0.85, at 71.5° F. and 1.5 mph wind; for net body heat produced from walking 4 mph, 2.11, at 67° F. and 4 mph wind; and for net body heat produced from running at an 8 minute per mile pace, 4.37, at 56° F. and 7.5 mph wind. In each instance the wind velocity is the *average effective wind* on the skin surface as a convective cooling factor resulting from the combination of air velocity and physical movement speed.

Strictly for layout design and not a programmed formula, the referred evaporative heat load requirement scale 2 (FIG. 1) and the co-radial aligned heat load requirement radius 2a of the heat load requirement versus evaporative cooling capacity grid (FIG. 9), are established on a logarithmic scale to provide simple physical spacing on both the scale and equivalent temperature line overlay 26 consistent with the functional relationship involved. Similary, the wind velocity scales 19 (FIG. 7) and 19a (FIG. 5) are proportional to $V^{.3}$ or the resulting convective cooling capacity. The relative humidity scale 29 (FIG. 10) and relative humidity radius 29a (FIG. 9) are linear.

The seven STEPS of entering and processing data in the calculator are summarized in abbreviated written instructions on the front and back panels of the calculator. A table of benchmark Heat Stress Temperatures and related environmental sensation and heat strain is printed on the front panel to guide the operator in properly interpreting equivalent temperatures.

It is noted that the instant invention was designed for a specific set of standard conditions which include the physiological response of a male of average weight, build, and age, dressed in light summer garments of 0.5 clo. However, the present calculator could be easily modified for appropriate use in connection with other standard inputs without altering the basic design features.

While particular embodiments of the present invention have been shown and described, it is apparent that changes and modifications may be made without departing from this invention in its broader aspects; and therefore, the aim in the appended claims is to cover all such changes and modifications as fall within the true spirit and scope of this invention.

What is claimed is:

1. A heat stress calculator for determining human heat stress or thermal discomfort reported as an equivalent temperature for any given summer air temperature, relative humidity, wind velocity, sky condition, time-of-day, terrain, and individual physical activity level, said calculator comprising in combination:

a stationary body front panel of square form having a central axis base and circular notched left edge and including:

(a) a cut out section of arcuate form, centrally positioned in the lower half, having inscribed immediately adjacent to the outer cicumference thereof, a 2nd input wind velocity scale;

(b) a transparent or cut out center window of rectangular form, centrally positioned in the upper half, having inscribed immediately adjacent to the left side thereof, a referred heat load scale, and further inscribed at the top left corner thereof a equivalent temperature arrow;

(c) a transparent or cut out left window of rectangular form, positioned diagonally to the left of center in the upper half, having inscribed immediately adjacent and central to the lower edge thereof, a heat load arrow;

(d) a transparent or cut out right window of rectangular form, positioned diagonally to the right of center in the upper half, having inscribed immediately adjacent and central to the lower edge thereof, a cooling capacity arrow;

a stationary body back panel of square form and circular notched right edge integral to the said body front panel at the bottom and folded along the common line against the said front panel, and including a centrally positioned transparent or cut out section of interruped circular form of two radii, the discontinuity forming a left and right physical activity stop, and having inscribed immediately adjacent to the lower circumference thereof, a physical activity scale, and having further inscribed immediately adjacent to the upper circumference thereof, space a sky scale;

a stationary body intermediate panel of substantially triangular form integral to the said body front panel at the top and folded along the common line against the front panel, having a central axis base and having inscribed a centrally positioned circular solar heat load scale;

a first disc element of essentially circular form having a central axis and mounted for rotation movement immediately below said body back panel and including:

(a) an inscribed grid of 1st input wind velocity versus convective cooling capacity circumference with 1st input temperature line overlay, in operative registration with a physical activity arrow inscribed immediately adjacent to the outer circumference;

(b) a physical activity tab with side stops in operative registration with counterpart said stops on said body rear panel; said physical activity tab extends above said body back panel;

a second disc element of circular form having a central axis and mounted for rotation movement immediately above said first disc with the top half located below said body intermediate panel and the bottom half located above said body back panel, and including:

(a) an inscribed circular body evaporative heat load requirement scale located inwardly of the outside circumference and positioned to be read from said left window of said body front panel, and in operative registration, a solar heat gain arrow inscribed on a solar tab, the said solar tab folded over to position said radiation arrow on the reverse side of said second disc element;

(b) a transparent or cut out window of arcuate form to permit visual display of said first input temperature line overlay of said first disc element;

(c) an extended circumference section in operative registration with said stops on a stationary body back panel, to limit rotation of said third disc;

a third disc element of circular form having a central axis and mounted for rotation immediately above said second disc with the top half located immediately below said body intermediate panel and including:

(a) a transparent or cut out perpendicular window of rectangular form positioned to read said first input temperature line overlay of said first disc, and having inscribed immediately adjacent to the left edge thereof, a 1st input wind velocity scale, and further inscribed at the top left corner thereof, a 1st input temperature arrow;

(b) a cut out solar slot of arcuate form having inscribed immediately adjacent to the inner circumference, a referred solar heat gain scale in operative registration with said first input temperature arrow. The said solar tab of said second rotating disk extends through said solar slot;

a fourth disc element of substantially rhombic form having a central axis located in the lower quadrant, and mounted for rotation movement between the upper halves of said body back panel and body intermediate panel and including:

(a) a circular inscribed time-of-day scale located inwardly of the outside circumference and in operative registration with said sky scale and said solar heat load scale on said body intermediate panel;

(b) a transparent or cut out horizontal window of rectangular form centrally positioned to read said solar heat gain scale on said body intermediate panel, having inscribed immediately adjacent to the lower edge thereof, a terrain scale in operative registration with said solar heat gain scale;

a fifth disc element of circular form having a central axis and mounted for rotation below said body front panel and including:

(a) an inscribed circular environment evaporative cooling capacity scale located inwardly of the outside circumference and positioned to be read from said right window of said body front panel, in operative registration with;

(b) an inscribed grid of linear scaled relative humidity radius and environment evaporative cooling rate circumference with 2nd input temperature line overlay;

(c) an inscribed grid of body evaporative heat load radius versus environment evaporative cooling capacity circumference with equivalent temperature line overlay positioned to be read from said central window of said body front panel;

(d) a cut out slot of arcuate form to permit visual display of the said body evaporative heat load requirement scale on said second disc;

a sixth disc element of essentially circular form having a central axis and mounted for rotation between said fifth disc element and said body front panel and including:

(a) a transparent or cut out perpendicular window of rectangular form centrally positioned in the lower half to read said 2nd input temperatue line overlay, having inscribed immediately adjacent to the left side thereof, a linear relative humidity scale, and further inscribed at the top left corner thereof a 2nd input temperature arrow;

(b) a wind arrow centrally located below and in operative registration with said perpendicular window and inscribed immediately adjacent to the outer circumference;

whereby the positioning of a selected one of said time-of-day values by a selected one of said sky conditions will operatively locate said solar heat load scale adjacent said terrain scale so as to display the correct solar radiation heat gain opposite a selected one of said terrain conditions; and, whereby the positioning of said solar radiation arrow by said correct solar radiation heat gain on said referred solar heat gain scale, and the positioning of said physical activity arrow by a selected one of said physical activity levels, and the positioning of a selected one of said wind velocity values by a selected one of adjacent said 1st input temperature lines at said 1st input temperature arrow, will operatively locate said body evaporative heat load requirement scale so as to display the correct heat load rate opposite said heat load arrow; and, whereby the positioning of said wind velocity arrow by a selected one of said wind velocity values, and the positioning of a selected one of said relative humidity values by a selected one of adjacent said 2nd input temperature lines at said 2nd input temperature arrow, will operatively locate said environment evaporative cooling capacity scale so as to display the correct cooling capacity rate opposite said cooling capacity arrow, and will operatively locate said equivalent temperature line overlay so as to display the correct equivalent temperature line opposite said correct heat load rate on said referred heat load scale at said equivalent temperature arrow.

2. The heat stress calculator as described in claim 1 wherein said sky, said time-of-day, said terrain, and said solar heat load, are equal angular logarithmic scales; said referred solar heat load, said net body heat production, said convective cooling capacity circumference, and said body evaporative heat load requirement, are equal angular linear scales where 12° equals a heat transfer rate of 10%; said 2nd input wind velocity, said environment evaporative cooling capacity, said environment evaporative cooling capacity circumference, and said environment evaporative cooling capacity circumference, are equal angular logarithmic scales; said 1st input wind velocity and in co-radial alignment with said 1st input wind velocity radius are equal scales of wind velocity to the 0.3 power; said relative humidity and in co-radial alignment said relative humidity radius are equal linear scales; and said referred heat load and in co-radial alignment with said heat gain radius are equal logarithmic scales.

3. The heat stress calculator as described in claim 1 wherein said environment evaporative cooling capacity, said environment evaporative cooling capacity circumference, said environment evaporative cooling capacity circumference, said solar heat gain, said referred solar heat gain, said net body heat production, said convective cooling circumference, said body evaporative heat load requirement, said referred heat load, and said heat load radius scales are expressed as a percent heat transfer rate, with 100% equal to 435 watts per square meter of skin surface for an average male; this level of heat transfer being the maximum evaporative cooling capacity of the human body under ideal thermal conditions as limited by sweat production and evaporation.

4. The heat stress calculator as described in claim 1 wherein heat stress is reported as an equivalent temperature which produces the same heat stress under standard moderate thermal and physical activity conditions as that resulting from the conditions actually experienced; the standard conditions being relative humidity, 35 percent; wind velocity, 2.5 mph; sun, hazy; time, 1 pm; terrain, grass; and physical activity, walking 2.5 mph; these standard conditions and air temperature of 70° F. resulting in zero, heat stress.

5. The heat stress calculator as described in claim 1 wherein heat stress is measured by sweat rate plotted as isohids on a psychometric chart which represent equivalent temperature lines when the abscissa air vapor pressure is converted to associated environment evaporative cooling capacity at standard wind velocity of 2.5 mph; and the ordinate air temperature is converted to associated body evaporative heat load requirement at standard wind 2.5 mph, sky condition hazy, time-of-day 1 pm, terrain grass, and physical activity walking 2.5 mph; equivalent temperature lines being labeled according to the temperature where the isohid intersects the standard relative humidity line of 35 percent, standard conditions have been selected so that the body's evaporative heat load requirement is zero at 70° F.

6. The heat stress calculator as described in claim 1 is calibrated by empirical evidence to equal zero body evaporative heat load requirement, by adjusting convective cooling to equal solar heat gain under standard conditions plus net body heat production under various recognized thermal conditions and physical activity levels, as illustrated by the following example ratios for a standard solar heat gain of 1.00 at 1 pm, haze sun, and grass terrain, net body heat production of 1.38 from walking 2.5 mph, convective cooling equals 2.38 at 70° F. and wind velocity of 2.5 mph; net body heat production of 0.85 from standing, convective cooling equals 1.85 at 71.5° F. and wind velocity of 1.5 mph; net body heat production from running at an 8 minute per mile pace, 4.37, convective cooling equals 5.37 at 56° F. and 7.5 mph wind.

7. The heat stress calculator as described in claim 1 wherein said physical activity scale in mets of energy expenditure, or metabolism, is calibrated to equal net body heat production—said metabolism less work performed less heat stored in the body, less heat loss from pulmonary respiration; said work performed and said heat storage being ellipitically shaped exponential functions (increasing at a decreasing rate) of said metabolism; said heat loss from pulmonary ventilation equalling 7.5 percent of said metabolism.

8. The heat stress calculator as described in claim 1 wherein clothing, sex, age, body weight, rest breaks once per hour have been programmed as fixed values.

* * * * *